(12) United States Patent
Kwon et al.

(10) Patent No.: US 11,974,834 B2
(45) Date of Patent: May 7, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Ui Kun Kwon, Hwaseong-si (KR); Chang Soon Park, Chungju-si (KR); Seung Keun Yoon, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 933 days.

(21) Appl. No.: 16/885,894

(22) Filed: May 28, 2020

(65) Prior Publication Data

US 2021/0177287 A1 Jun. 17, 2021

(30) Foreign Application Priority Data

Dec. 13, 2019 (KR) .................... 10-2019-0166985

(51) Int. Cl.
*A61B 5/021* (2006.01)
*A61B 5/00* (2006.01)
(Continued)

(52) U.S. Cl.
CPC ...... *A61B 5/02125* (2013.01); *A61B 5/02007* (2013.01); *A61B 5/02233* (2013.01);
(Continued)

(58) Field of Classification Search
CPC ............. A61B 5/02007; A61B 5/0205; A61B 5/021–02125; A61B 5/024;
(Continued)

(56) References Cited

U.S. PATENT DOCUMENTS 4,930,517 A 6/1990 Cohen et al.
8,343,049 B2 * 1/2013 Hatlestad ............... A61B 5/1116
607/18

(Continued)

FOREIGN PATENT DOCUMENTS

CN 107249441 A 10/2017
JP 200 2008-234009 A 10/2008
(Continued)

OTHER PUBLICATIONS

Communication dated Nov. 30, 2020 issued by the European Patent Office in European Application No. 20191801.8.
(Continued)

*Primary Examiner* — Navin Natnithithadha
*Assistant Examiner* — Alice Ling Zou
(74) *Attorney, Agent, or Firm* — Sughrue Mion, PLLC

(57) ABSTRACT

An apparatus for estimating bio-information may include: a processor configured to measure a current time interval between a plurality of element waveforms of the pulse wave signal, determine whether a current measurement posture of the user corresponds to a reference posture based on the current time interval of the plurality of element waveforms, and estimate the bio-information based on a determination of whether the current measurement posture corresponds to the reference posture.

20 Claims, 14 Drawing Sheets

(51) Int. Cl.
   *A61B 5/02* (2006.01)
   *A61B 5/022* (2006.01)
   *A61B 5/11* (2006.01)

(52) U.S. Cl.
   CPC ............ *A61B 5/1116* (2013.01); *A61B 5/681* (2013.01); *A61B 5/7246* (2013.01); *A61B 5/7435* (2013.01); *A61B 2560/0223* (2013.01)

(58) Field of Classification Search
   CPC ............ A61B 5/02405; A61B 5/02416; A61B 5/02438; A61B 5/1116; A61B 5/6801; A61B 5/681; A61B 5/7221; A61B 5/7239; A61B 5/7246; A61B 5/7235; A61B 2560/0223; A61B 5/2405; A61B 5/70; A61B 5/72; A61B 5/11
   See application file for complete search history.

(56) References Cited

U.S. PATENT DOCUMENTS

| | | | |
|---|---|---|---|
| 10,299,690 | B2 | 5/2019 | Choi et al. |
| 10,602,935 | B2 | 3/2020 | Fuke et al. |
| 2002/0026121 | A1 | 2/2002 | Kan |
| 2008/0228046 | A1 | 9/2008 | Futatsuyama et al. |
| 2011/0144456 | A1 | 6/2011 | Muhlsteff et al. |
| 2013/0018272 | A1* | 1/2013 | Hori ............... A61B 5/021 600/501 |
| 2016/0302677 | A1 | 10/2016 | He |
| 2017/0150893 | A1 | 6/2017 | McCombie et al. |
| 2017/0172431 | A1 | 6/2017 | Kim et al. |
| 2017/0296076 | A1* | 10/2017 | Mahajan ............... A61B 5/002 |
| 2018/0020990 | A1 | 1/2018 | Park et al. |
| 2018/0256044 | A1* | 9/2018 | Goodman .......... A61B 5/02125 |
| 2018/0263518 | A1 | 9/2018 | Shimuta |
| 2019/0021611 | A1* | 1/2019 | Kwon ................. A61B 5/1128 |
| 2019/0200932 | A1 | 7/2019 | Noh et al. |
| 2019/0274555 | A1* | 9/2019 | Park ................... A61B 5/02116 |

FOREIGN PATENT DOCUMENTS

| | | | | |
|---|---|---|---|---|
| JP | 2016-131825 | A | 7/2016 | |
| JP | 2017136240 | A | 8/2017 | |
| KR | 10-2014-0003820 | A | 1/2014 | |
| KR | 10-2017-0073051 | A | 6/2017 | |
| KR | 10-2019-0081650 | A | 7/2019 | |
| WO | WO-2015101698 | A2 * | 7/2015 | ........... A61B 5/0205 |
| WO | 2016/034907 | A1 | 3/2016 | |

OTHER PUBLICATIONS

Zaidi, S.N., et al., "Orthostatic stress and area under the curve of photoplethysmography waveform" Biomedical Physics & Engineering Express, vol. 2, May 11, 2016, pp. 1-13 (14 pages).

Linder, S., et al., "Using The Morphology of Photoplethysmogram Peaks to Detect Changes in Posture", Journal of Clinical Monitoring and Computing, 2006, vol. 20, No. 3, pp. 151-158.

Office Action dated Nov. 30, 2023 by the State Intellectual Property Office of People's Republic of China in corresponding Chinese Patent Application 202010553528.7.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2019-0166985, filed on Dec. 13, 2019, in the Korean Intellectual Property Office, the entire disclosure of which is incorporated herein by reference for all purposes.

BACKGROUND

1. Field

Example embodiments relate to non-invasively estimating bio-information.

2. Description of Related Art

Recently, with the aging population, soaring medical costs, and shortage of medical personnel for specialized medical services, research is being actively conducted on information technology (IT)-medical convergence technologies, in which IT technology and medical technology are combined. Particularly, monitoring of the health condition of the human body is not limited to medical institutions, but is expanding to mobile healthcare fields that may monitor a user's health condition anywhere and anytime in daily life at home or office. Typical examples of bio-signals, which indicate the health condition of individuals, include an electrocardiography (ECG) signal, a photoplethysmogram (PPG) signal, an electromyography (EMG) signal, and the like, and various bio-signal sensors have been developed to measure these signals in daily life. Particularly, a PPG sensor may estimate blood pressure of a human body by analyzing a shape of pulse waves which reflect a cardiovascular status and the like.

SUMMARY

According to an aspect of an example embodiment, there is provided an apparatus for estimating bio-information, the apparatus including: a pulse wave sensor configured to measure a pulse wave signal from a user; and a processor configured to measure a current time interval between a plurality of element waveforms of the pulse wave signal, determine whether a current measurement posture of the user corresponds to a reference posture based on the current time interval of the plurality of element waveforms, and estimate the bio-information based on a determination of whether the current measurement posture corresponds to the reference posture.

The processor may be further configured to determine a reference time interval between a plurality of reference element waveforms of a reference pulse wave signal that is measured in the reference posture, and determine whether the current measurement posture of the user corresponds to the reference posture, based on a difference between the reference time interval and the current time interval.

The processor may be further configured to compare the difference between the reference time interval and the current time interval with a predetermined threshold value, and determine that the current measurement posture does not correspond to the reference posture based on the difference between the reference time interval and the current time interval being greater than the predetermined threshold value.

The processor may be further configured to determine whether the current measurement posture corresponds to the reference posture further based on a difference between a current heart rate measured in the current measurement posture and a reference heart rate measured in the reference posture.

The processor may be further configured to compare a first difference between the reference time interval and the current time interval with a first threshold value, compare a second difference corresponding to the difference between the current heart rate and the reference heart rate with a second threshold value, and determine whether the current measurement posture corresponds to the reference posture, based on comparisons between the first difference and the first threshold value, and between the second difference and the second threshold value.

The plurality of element waveforms may include at least two or more of a first element waveform related to a propagation wave, and a second element waveform and a third element waveform related to a reflection wave.

The processor may be further configured to obtain a differential signal of the measured pulse wave signal, and obtain times of the plurality of element waveforms by analyzing a local minimum point or a local maximum point of a waveform of the obtained differential signal.

The processor may be further configured to extract one or more features from the measured pulse wave signal, and estimate the bio-information based on the one or more extracted features.

The processor may be further configured to obtain an error correction value based on a difference between the current measurement posture and the reference posture, and correct the estimated bio-information based on the error correction value.

The processor may be further configured to obtain the error correction value based on at least one of a first difference between the current time interval and a reference time interval, and a second difference between a current heart rate measured in the current measurement posture and a reference heart rate measured in the reference posture. The reference time interval may be an interval between a plurality of reference element waveforms of a reference pulse wave signal that is measured in the reference posture.

Based on the error correction value exceeding a threshold value, the processor may be further configured to determine the threshold value to be the error correction value.

The bio-information may include one or more of blood pressure, vascular age, arterial stiffness, aortic pressure waveform, vascular compliance, stress index, and fatigue level.

The apparatus may further include a display, wherein the processor may be further configured to provide, on the display, guide information for guiding the user to change the current posture to the reference posture, based on the current measurement posture not corresponding to the reference posture.

The apparatus may further include a speaker, wherein the processor may be further configured to provide, through the speaker, guide information for guiding the user to change the current posture to the reference posture, based on the current measurement posture not corresponding to the reference posture According to an aspect of an example embodiment, there is provided a method of estimating bio-information, the method including: obtaining a pulse wave signal from a user; measuring a current time interval between a plurality of element waveforms of the pulse wave signal; determining whether a current measurement posture of the user corresponds to a reference posture based on the current time interval of the plurality of element waveforms; and estimating the bio-information based on a determination of whether the current measurement posture corresponds to the reference posture.

The determining whether the current measurement posture corresponds to the reference posture may include: determining a reference time interval between a plurality of reference element waveforms of a reference pulse wave signal that is measured in the reference posture; and determining whether the current measurement posture of the user corresponds to the reference posture, based on a difference between the reference time interval and the current time interval.

The determining whether the current measurement posture corresponds to the reference posture may include: comparing the difference between the reference time interval and the current time interval with a predetermined threshold value; and determining that the current measurement posture does not correspond to the reference posture based on the difference between the reference time interval and the current time interval being greater than the predetermined threshold value.

The determining whether the current measurement posture corresponds to the reference posture may include: determining whether the current measurement posture corresponds to the reference posture further based on a difference between a current heart rate measured in the current measurement posture and a reference heart rate measured in the reference posture.

The determining whether the current measurement posture corresponds to the reference posture may include: comparing a first difference between the reference time interval and the current time interval with a first threshold value; compare a second difference corresponding to the difference between the current heart rate and the reference heart rate, with a second threshold value; and determining whether the current measurement posture corresponds to the reference posture, based on comparisons between the first difference and the first threshold value, and between the second difference and the second threshold value.

The estimating the bio-information may include: extracting one or more features from the measured pulse wave signal; and estimating the bio-information based on the extracted one or more features.

The estimating the bio-information may further include: obtaining an error correction value based on a difference between the current measurement posture and the reference posture; and correcting the estimated bio-information based on the error correction value.

The obtaining the error correction value may include: obtaining the error correction value based on at least one of a first difference between the current time interval and a reference time interval and a second difference between a current heart rate measured in the current measurement posture and a reference heart rate measured in the reference posture. The reference time interval is an interval between a plurality of reference element waveforms of a reference pulse wave signal that is measured in the reference posture.

The obtaining the error correction value may include, based on the error correction value exceeding a threshold value, determining the threshold value to be the error correction value.

BRIEF DESCRIPTION OF THE DRAWINGS

The above and/or other aspects will be more apparent from the following description of example embodiments, with reference to the accompanying drawings, in which.

DETAILED DESCRIPTION

Figure 1:
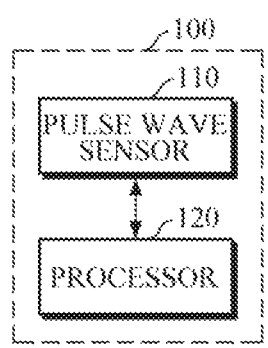
FIG. 1 is a block diagram illustrating an apparatus for estimating bio-information according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit for processing at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an apparatus and method for estimating bio-information will be described in detail with reference to the accompanying drawings. The apparatus for estimating bio-information according to the example embodiments may be embedded in a terminal, such as a smartphone, a tablet PC, a desktop computer, a laptop computer, and the like, or may be manufactured as an independent hardware device. In this case, the independent hardware device may be a wearable device worn on an object OBJ, and examples of the wearable device may include a wristwatch-type wearable device, a bracelet-type wearable device, a wristband-type wearable device, a ring-type wearable device, a glasses-type wearable device, a headband-type wearable device, or the like, but the wearable device is not limited thereto.

Figure 2:
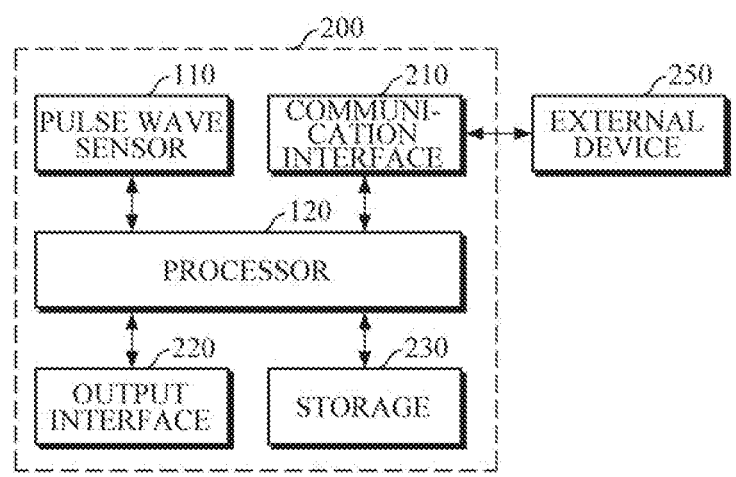
FIG. 2 is a block diagram illustrating an apparatus for estimating bio-information according to another example embodiment.

FIG. 1 is a block diagram illustrating an apparatus 100 for estimating bio-information according to an example embodiment. FIG. 2 is a block diagram illustrating an apparatus 200 for estimating bio-information according to another example embodiment.

Referring to FIGS. 1 and 2, the apparatuses 100 and 200 for estimating bio-information include a pulse wave sensor 110 and a processor 120.

The pulse wave sensor 110 may measure a pulse wave signal, including a photoplethysmography (PPG) signal, from an object. The pulse wave sensor 110 may include a light source which emits light onto the object to detect an optical signal from the object; and a detector which detects scattered or reflected light when light emitted by the light source is scattered or reflected from body tissue such as a skin surface or blood vessels of the object. The light source may include a light emitting diode (LED), a laser diode (LD), a phosphor, and the like, but examples of the light source are not limited thereto. The detector may include a photo diode, a photo transistor (PTr), an image sensor (e.g., CMOS image sensor), and the like, but examples of the detector not limited thereto. The pulse wave sensor 110 may have various structures, such as a structure including a plurality of light sources and one detector, or a structure including an array of pairs of light sources and detectors, and the like, without specific limitation.

In particular, the object may be a body part which comes into contact with or is adjacent to the pulse wave sensor 110, and may be a body part where the pulse wave signals may be easily measured. For example, the object may be a skin area of a wrist which is adjacent to a radial artery, or a skin area of the body where veins or capillaries are located. However, examples of the object are not limited thereto, and may include a distal portion of the body, such as fingers, toes, and the like, where blood vessels are densely located.

The processor 120 may be electrically connected to the pulse wave sensor 110. In response to a request for estimating bio-information, the processor 120 may control the pulse wave sensor 110, and may receive a pulse wave signal from the pulse wave sensor 110. The request for estimating bio-information may be input from a user, or may be generated at predetermined intervals. Upon receiving an electrical pulse wave signal from the pulse wave sensor 110, the processor 120 may perform preprocessing, such as filtering the pulse wave signal for removing noise, amplifying the pulse wave signal, converting the signal into a digital signal, smoothing the signal, and the like.

Upon receiving the pulse wave signal, the processor 120 may obtain cardiovascular features from the pulse wave signal, and may estimate bio-information by using the obtained features. In particular, the bio-information may include cardiovascular information such as blood pressure, vascular age, arterial stiffness, aortic pressure waveform, vascular compliance, stress index, fatigue level, and the like. For convenience of explanation, the following description will be given using blood pressure as an example if necessary.

Generally, a variation in Mean Arterial Pressure (MAP) is proportional to cardiac output (CO) and total peripheral resistance (TPR), as represented by the following Equation 1.

$$\Delta MAP = CO \times TPR \quad \text{[Equation 1]}$$

Herein, ΔMAP denotes a difference in MAP between the left ventricle and the right atrium, in which MAP of the right atrium is generally in a range of 3 mmHg to 5 mmHg, such that the MAP in the right atrium is similar to MAP in the left ventricle or MAP of the upper arm. If absolute actual CO and TPR values are known, MAP may be obtained from the aorta or the upper arm. However, it may be difficult to estimate absolute CO and TPR values based on a bio-signal at a high accuracy, according to conventional bio-information estimation methods.

The processor 120 may obtain a feature associated with cardiac output (CO) and a feature associated with total peripheral resistance (TPR) from a pulse wave signal. Here, the feature associated with cardiac output (CO) may be a feature value which shows an increasing or decreasing trend in proportion to an actual CO value which relatively increases or decreases when an actual TPR value does not change significantly compared to a resting state. Further, the feature associated with total peripheral resistance (TPR) may be a feature value which shows an increasing or decreasing trend in proportion to an actual TPR value which relatively increases or decreases when an actual CO value does not change significantly compared to a resting state.

The processor 120 may obtain cardiovascular features by analyzing a waveform of the measured pulse wave signal. For example, by analyzing the waveform of the pulse wave signal, the processor 120 may obtain an area under the curve or waveform of the pulse wave signal, including heart rate information, as the feature associated with cardiac output (CO). Further, the processor 120 may obtain a ratio between an amplitude of a propagation wave and an amplitude of a first reflection wave as the feature associated with total peripheral resistance (TPR). However, the features are not limited thereto, and the processor 120 may obtain cardiovascular features further based on a shape of the waveform of the pulse wave signal, time and amplitude values of a maximum point of the pulse wave signal, time and amplitude values of a minimum point of the pulse wave signal, a duration of the pulse wave signal, components of individual element waveforms which constitute the waveform of the pulse wave signal (e.g., time and amplitude values of the element waveforms), information related to an internally dividing point between the obtained values, and the like.

Referring back to FIG. 2, the apparatus 200 for estimating bio-information may further include a communication interface 210, an output interface 220, and a storage 230.

The communication interface 210 may communicate with an external device 250 by using wired or wireless communication techniques under the control of the processor 120, and may transmit and receive various data to and from the external device 250. For example, the communication interface 210 may transmit a bio-information estimation result to the external device 250, and may receive, from the external device 250, a variety of reference information required for estimating bio-information. For example, the communication interface 210 may receive reference blood pressure measured by a cuff manometer, a bio-information estimation model, and the like from the external device 250. In this case, the external device 250 may include a cuff manometer, and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, and 5G telecommunications, and the like. However, this is merely exemplary and is not intended to be limiting.

The output interface 220 may output results processed by the pulse wave sensor 110 and the processor 120. For example, the output interface 220 may visually output an estimated bio-information value using a display. Alternatively, the output interface 220 may output the estimated bio-information value in a non-visual manner by voice, vibrations, tactile sensation, and the like, using a speaker, a haptic module, or the like. By dividing a display area into two or more areas according to a setting, the output interface 220 may output a pulse wave signal graph used for estimating bio-information, a bio-information estimation result, and the like, in a first area; and may output a bio-information estimation history in the form of graphs in a second area. In this case, if an estimated bio-information value falls outside a predetermined normal range, the output interface 220 may output warning information in various manners, such as highlighting an abnormal value in red and the like, displaying the abnormal value along with a normal range, outputting a voice warning message, adjusting a vibration intensity, and the like.

The storage 230 may store processing results of the pulse wave sensor 110 and the processor 120. Further, the storage 230 may store a variety of reference information required for estimating bio-information. For example, the reference information may include reference blood pressure, a bio-information estimation model, an equation for calculating an error correction value, a bio-information estimation interval, as well as user characteristics including a user's age, sex, health condition, and the like, but is not limited thereto.

In particular, the storage 230 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EE-PROM), a Programmable Read Only Memory (PROM), a magnetic memory, a magnetic disk, and an optical disk, and the like, but is not limited thereto.

FIGS. 3A to 3D are diagrams explaining individual element waveforms of a pulse wave signal.

Figure 3A:
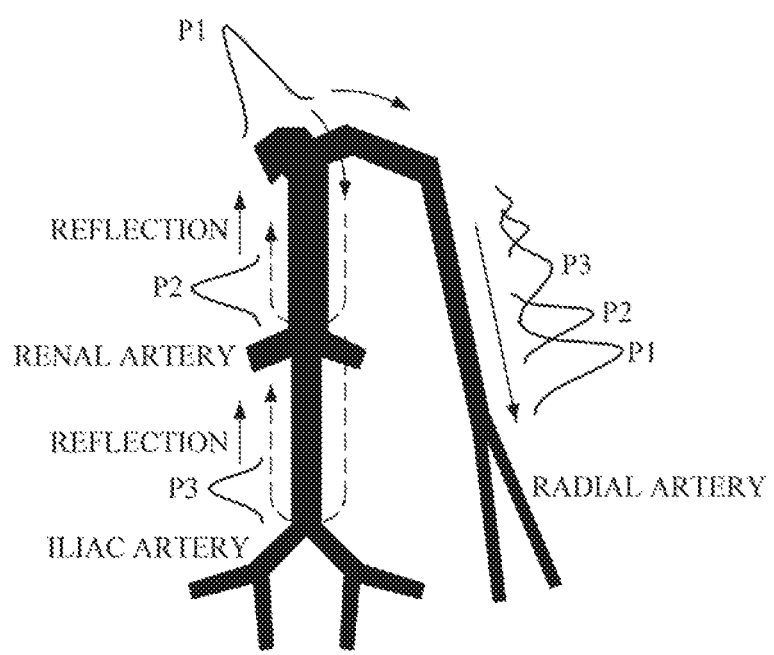
FIGS. 3A to 3D are diagrams explaining element waveforms of a pulse wave signal.
Figure 3B:
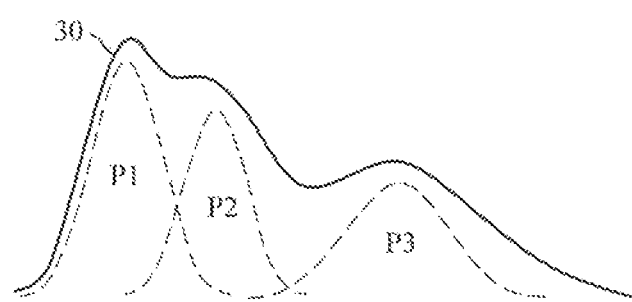

Referring to FIGS. 3A and 3B, a pulse wave signal 30 is generally formed by superposition of a propagation wave P1, which moves from the heart to the distal end of the body or branching points in the blood vessels by blood ejection from the left ventricle, and reflection waves P2 and P3 which return from the distal end of the body or the branching points of the blood vessels. In this case, the propagation wave P1 is related to heart characteristics and the reflection waves P2 and P3 are related to vascular characteristics. As illustrated in FIGS. 3A and 3B, the waveform of the pulse wave signal 30 is composed of individual component waveforms, such as, for example, the propagation wave P1 which is generated by blood ejection from the left ventricle, a first reflection wave P2 which is mainly reflected from the renal arteries, a second reflection wave P3 which is mainly reflected from the iliac arteries, and the like. Information related to blood pressure may be included in a time interval and/or an amplitude ratio between the propagation wave and the reflection wave which are included in the waveform of the pulse wave signal 30.

The processor 120 may extract components of the element waveforms related to the propagation wave and the reflection wave (e.g., time and amplitude values of a first element waveform, time and/or amplitude values of a second element waveform, and the like), and may obtain features for estimating blood pressure based on each of the extracted components of the element waveforms. In this manner, the processor 120 may estimate bio-information based on the features obtained from the pulse wave signal 30.

The waveform of the pulse wave signal 30 may generally change with a blood pressure measurement posture, such that when blood pressure is estimated based on the waveform of the pulse wave signal 30, there may be an error in the estimated blood pressure value. For example, compared to a blood pressure value in a middle part of the aorta which is measured at a height of the heart, blood pressure values in each part of the aorta, measured in a standing position or a sitting position, are increased every time the height of hydrostatic pressure is lowered. As described above, when pulse waves are transmitted within the blood vessels, pressure in the blood vessels in the transmission path is changed with posture, thus affecting the pulse wave velocity. That is, when an individual's posture is changed from a sitting position or a standing position to a lying position, blood pressure is reduced even in the renal and iliac arteries where reflections of the pulse waves usually take place, and the pulse wave velocity may also be reduced.

Figure 3C:
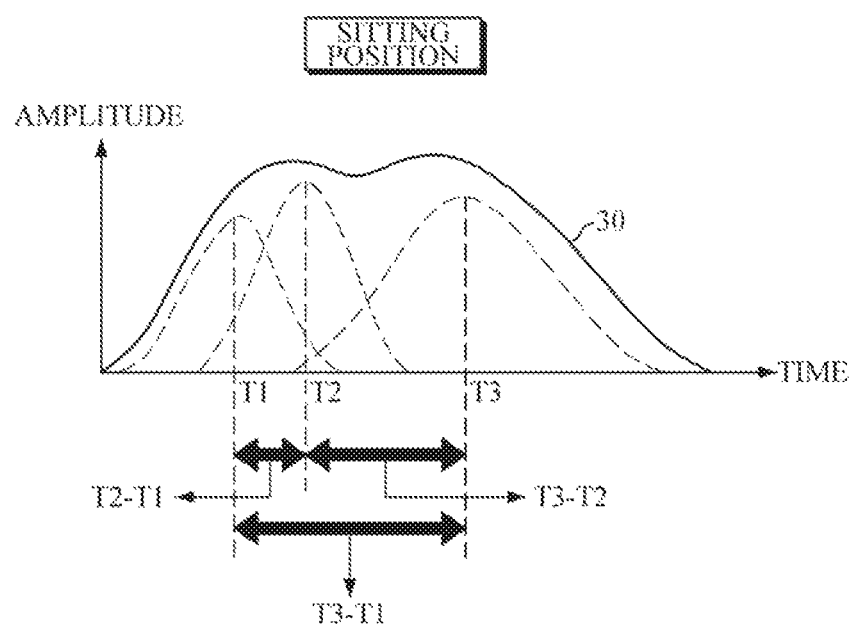
Figure 3D:
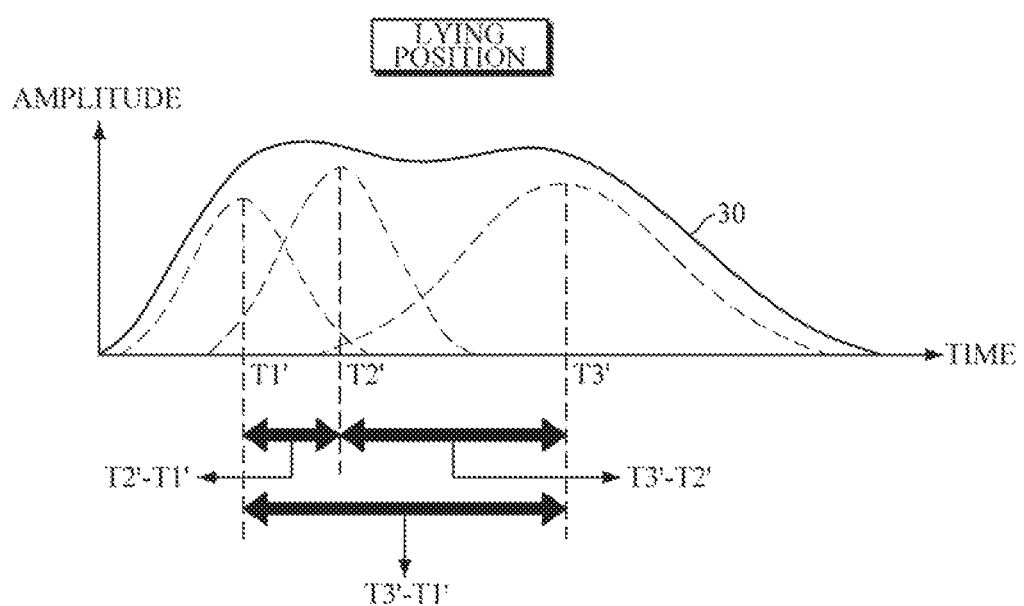

For example, FIG. 3C illustrates an example of time intervals between element waveforms in a normal sitting position, and FIG. 3D illustrates an example of time intervals between element waveforms in a lying position. In the example embodiment, as illustrated in FIGS. 3C and 3D, by using changes in time intervals T3−T1, T2−T1, and T3−T2 between a peak time T1 of the propagation wave and peak times T2 and T3 of the first and second reflection waves, the processor 120 may detect a change in a user's measurement posture. The processor 120 may obtain an estimated blood pressure value based on the detected change in posture, thereby allowing continuous measurements regardless of a user's measurement posture, and improving estimation accuracy.

Figure 4:
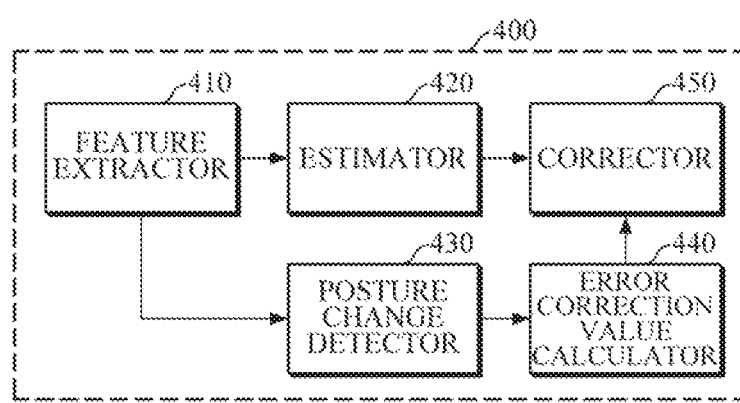
FIG. 4 is a block diagram illustrating a configuration of a processor according to an example embodiment.

FIG. 4 is a block diagram illustrating a configuration of a processor according to an example embodiment.

Referring to FIG. 4, the processor 400 according to an example embodiment includes a feature extractor 410, an estimator 420, a posture change detector 430, an error correction value calculator 440, and a corrector 450.

The feature extractor 410 may extract features for estimating bio-information based on a pulse wave signal 30. As described above, by analyzing the waveform of the pulse wave signal 30, the feature extractor 410 may obtain components of individual element waveforms which constitute the waveform of the pulse wave signal 30, and may extract a feature associated with cardiac output and a feature associated with total peripheral resistance by using the obtained components of individual element waveforms.

For example, the feature extractor 410 may obtain a differential signal (e.g., a second-order differential signal) of the pulse wave signal 30, and may obtain the components of individual element waveforms, related to the propagation wave and the reflection waves, by detecting a local maximum point/local minimum point of the waveform of the second-order differential signal. In this case, the order of differentiation is not specifically limited.

For example, the feature extractor 410 may extract a time at a first local minimum point of the second-order differential signal as a time component of a first element waveform related to the propagation wave. Further, the feature extractor 410 may obtain times at a second local minimum point and a third local minimum point as time components of a second element waveform and a third element waveform related to the reflection waves. As described above, upon obtaining the time component of the individual element waveforms, the feature extractor 410 may obtain an amplitude at a point, corresponding to the time of each element waveform in the waveform of the pulse wave signal 30, as an amplitude component of each element waveform.

However, the features are not limited to the aforementioned examples, and the feature extractor 410 may obtain features based further on an area of a predetermined interval of the waveform of the pulse wave signal 30, time and/or amplitude values at a point where an amplitude is maximum in the waveform of the pulse wave signal 30, time and/or amplitude values located at the right and left points of the maximum amplitude point and having a predetermined ratio to the maximum amplitude value, a heart rate, and the like.

The estimator 420 may estimate bio-information by applying a bio-information estimation model based on the features extracted by the feature extractor 410. For example, the bio-information estimation model may be defined as a linear function as represented by the following Equation 2, but is not limited thereto, and may be defined by using various techniques such as non-linear regression analysis, neural network, and the like.

$$HP = SF \times F + OFF \qquad \text{[Equation 2]}$$

Herein, BP denotes an estimated blood pressure value, and F is associated with the feature value extracted by the feature extractor 410, and may be, for example, the feature value itself or a variation in bio-information at a bio-information estimation time compared to a calibration time. In this case, the variation in bio-information may be a variation in a feature value at the bio-information estimation time compared to a feature value at the calibration time, or a normalized value obtained by dividing the variation by the feature value at the calibration time. Further, SF denotes a value pre-defined by preprocessing, and may be a scaling element for scaling a value associated with the feature values. OFF may denote a measured bio-information value for calibration, which is measured at the calibration time by using an external apparatus for measuring bio-information.

Once the components of the individual element waveforms are extracted from the pulse wave signal 30, the posture change detector 430 may estimate a change in a current measurement posture at a measurement time of the pulse wave signal 30 compared to a reference posture at the calibration time, based on time intervals between the extracted individual element waveforms. The reference posture may be set for each user, and may be, for example, a sitting position, a standing position, and the like. However, the reference posture is not limited thereto, and may be set to a supine position, a side-lying position, a seated-reclining position, and the like by considering a user's various measurement environments, health condition, and the like.

The posture change detector 430 may compare reference time intervals between the element waveforms of the pulse wave signal 30, which are measured in the reference posture at the calibration time, with current time intervals between element waveforms of the pulse wave signal 30 obtained in the current measurement posture at the bio-information estimation time. If differences between the reference time intervals and the corresponding current intervals are greater than a predetermined reference value, the posture change detector 430 may determine that there is a change in posture. For example, compared to the first time intervals between the element waveforms of the pulse wave signal 30 in the reference posture, if a variation in the second time intervals between the element waveforms of the pulse wave signal 30 in the current measurement posture is greater than a predetermined threshold value, the posture change detector 430 may detect that the current measurement posture is changed to a posture, which causes a drop in blood pressure, compared to the reference posture.

Referring back to FIGS. 3C and 3D, the posture change detector 430 may compare a first reference time interval (i.e., T2−T1) between the peak time T1 of the propagation wave and the peak time T2 of the first reflection wave of the pulse wave signal 30, which is measured when the user is in the sitting position, with a first current time interval (i.e., T2'−T1') between the peak time T1' of the propagation wave and the peak time T2' of the first reflection wave of the pulse wave signal 30, which is measured when the user is in the lying position. The posture change detector 430 may compare a second reference time interval (i.e., T3−T2) between the peak time T2 of the first reflection wave and the peak time T3 of the second reflection wave of the pulse wave signal 30, which is measured when the user is in the sitting position, with a second current time interval (i.e., T3'−T2') between the peak time T2' of the first reflection wave and the peak time T3' of the second reflection wave of the pulse wave signal 30, which is measured when the user is in the lying position. The posture change detector 430 may compare a third reference time interval (i.e., T3−T1) between the peak time T1 of the propagation wave and the peak time T3 of the second reflection wave of the pulse wave signal 30, which is measured when the user is in the sitting position, with a third current time interval (i.e., T3'−T1') between the peak time T1' of the propagation wave and the peak time T3' of the second reflection wave of the pulse wave signal 30, which is measured when the user is in the lying position. The posture change detector 430 may determine a first difference value between the first reference time interval (i.e., T2−T1) and the first current time interval (i.e., T2'−T1'), a second difference value between the second reference time interval (i.e., T3−T2) and the second current time interval (i.e., T3'−T2'), and a third difference value between the third reference time interval (i.e., T3−T1) and the third current time interval (i.e., T3'−T1'). The posture change detector 430 may compare the first difference value, the second difference value, and the third difference value with a predetermined first threshold value, a predetermined second threshold value, and a predetermined third threshold value, respectively. The posture change detector 430 may determine the current posture (e.g., lying position) of the user is different from the reference posture (e.g., sitting position) when at least one of the first difference value, the second difference value, and the third difference value is greater than a corresponding one of the predetermined first threshold value, the predetermined second threshold value, and the predetermined third threshold value.

Further, in addition to the comparison of the time intervals between the element waveforms of the pulse wave signal 30, the posture change detector 430 may estimate a posture change based further on heart rate information. In this case, the heart rate information may include a heart rate in the reference posture at the calibration time, a heart rate in the current measurement posture at the bio-information estimation time, a variation in the heart rate at the bio-information estimation time compared to the heart rate at the calibration time, or a value obtained by normalizing the variation in the heart rate based on the heart rate at the calibration time, e.g., a value obtained by dividing the variation in the heart rate by the heart rate at the calibration time.

For example, in the current measurement posture compared to the reference posture, if a variation $\Delta$(T2–T1) in a time interval T2–T1 between a first element waveform and a second element waveform is greater than a first threshold value (e.g., 4), if a variation $\Delta$(T3–T1) in a time interval T3–T1 between a first element waveform and a third element waveform is greater than a second threshold value (e.g., 15), if a variation $\Delta$(T3–T2) in a time interval T3–T2 between the second element waveform and the third element waveform is greater than a third threshold value (e.g., 10), and if a value $\Delta HR_{norm}$, obtained by normalizing a variation in heart rate, is less than a fourth threshold value (e.g., 1.02), the posture change detector 430 may detect that the current measurement posture is changed to a posture, which causes a drop in blood pressure, compared to the reference posture.

Once the posture change detector 430 detects that the current measurement posture is changed due to mechanism of rise/fall of blood pressure compared to the reference posture, the error correction value calculator 440 may calculate an error correction value corresponding to the posture change.

For example, when the reference posture is a sitting posture or a standing posture, if the posture change detector 430 detects that a current measurement posture is changed to a lying posture which causes a fall in blood pressure, the error correction value calculator 440 may calculate an error correction value based on the heart rate information (e.g., a value obtained by normalizing the variation in the heart rate in the current measurement posture compared to the heart rate in the reference posture), as represented by the following Equation 3. However, Equation 3 is a non-limiting example, the error correction value is not specifically limited, and a time interval between the element waveforms may be further reflected.

$$EV = \min(e1 \times HR_{norm} + e2, e3) \quad \text{[Equation 3]}$$

Herein, EV denotes the error correction value; $HR_{norm}$ denotes a value obtained by normalizing the variation in heart rate based on the heart rate measured in the reference posture at the calibration time; e1, e2, and e3 are values pre-defined by preprocessing; and min denotes a function for calculating a minimum value.

If the posture change detector 430 does not detect a posture change, the error correction value calculator 440 may calculate an error correction value to be 0.

Once the error correction value is calculated, the corrector 450 may correct the estimated bio-information value which is estimated by the estimator 420. The following Equation 4 is an example of an error correction equation, in which an error correction value, calculated when the measurement posture is changed to a posture which causes a fall in blood pressure, is applied to the blood pressure estimation model of the above Equation 2. However, the error correction equation is not limited thereto.

$$BP = SF \times F + OFF - EV \quad \text{[Equation 4]}$$

Herein, EV denotes the error correction value calculated by the error correction value calculator 440, and BP denotes a final estimated blood pressure value, in which the error correction value is reflected.

Figure 5:
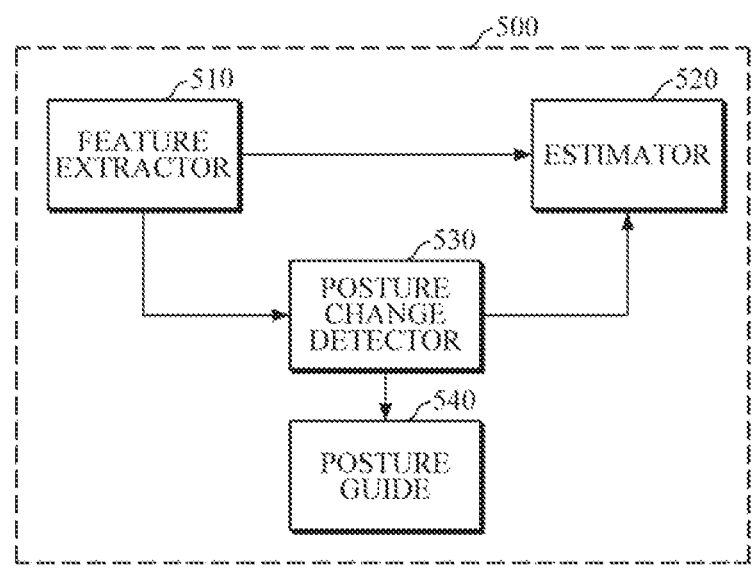
FIG. 5 is a block diagram illustrating a configuration of a processor according to another example embodiment.
Figure 6A:
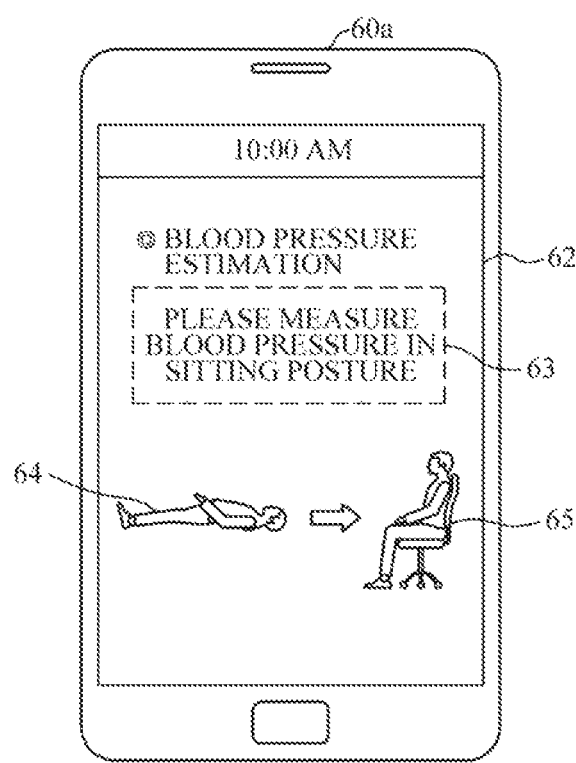
FIGS. 6A and 6B are diagrams illustrating examples of guiding a measurement posture.
Figure 6B:
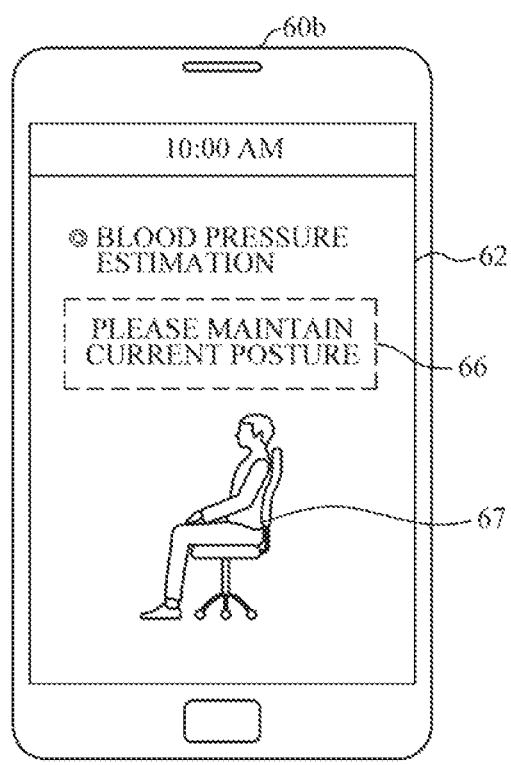

FIG. 5 is a block diagram illustrating a configuration of a processor according to another example embodiment. FIGS. 6A and 6B are diagrams illustrating examples of guiding a measurement posture.

Referring to FIG. 5, the processor 500 includes a feature extractor 510, an estimator 520, a posture change detector 530, and a posture guide 540.

Once the pulse wave sensor 110 acquires a pulse wave signal 30, the feature extractor 510 may extract features by analyzing a waveform of the pulse wave signal 30. For example, the feature extractor 510 may extract cardiovascular features based on components of individual element waveforms which constitute the waveform of the pulse wave signal 30, a total or partial area under the waveform of the pulse wave signal 30, a maximum amplitude value of the pulse wave signal 30, time and/or amplitude values located at the right and left points of the maximum amplitude point and having a predetermined ratio to the maximum amplitude value, and the like.

The posture change detector 530 may detect a change in a current measurement posture at a bio-information estimation time compared to a reference posture at a calibration time, based on time intervals between the individual element waveforms of the pulse wave signal 30 and/or heart rate information. In this case, the reference posture may be set for each user. The heart rate information may include a heart rate in the reference posture at the calibration time, a heart rate in the current measurement posture at the bio-information estimation time, a variation in the heart rate at the bio-information estimation time compared to the heart rate at the calibration time, or a value obtained by normalizing the variation in the heart rate based on the heart rate at the calibration time.

Upon determining that the current measurement posture is changed to a posture, which affects an estimated bio-information value compared to the reference posture, the posture change detector 530 may transmit a request for posture guide information to the posture guide 540, and may control the pulse wave sensor to re-measure the pulse wave signal 30.

The posture guide 540 may generate information for guiding a change in posture based on information on the posture change detected by the posture change detector 530. For example, when the posture change detector 530 detects that the measurement posture is changed compared to the reference posture, the guide information may include information, such as a visual image and/or a voice signal, for guiding a user to change the posture to the reference posture. Further, when the posture change detector 530 detects that the measurement posture is not changed, the guide information may include at least one of a visual image and a voice signal for guiding a user to maintain the measurement posture. The output interface 220 of FIG. 2 may output the guide information generated by the posture guide 540.

For example, referring to FIG. 6A, if a user's reference posture is a sitting posture, and the user's current measurement posture is a lying posture, the output interface 220 may output a text 63, such as "please measure blood pressure in a sitting posture," in a predetermined area of a display 62 of a mobile device 60a. Further, along with the text 63, the output interface 220 may simultaneously or separately output visual images 64 and 65 for inducing the user to change from the "lying posture" to the "sitting posture."

Referring to FIG. 6B, if a user's reference posture is a sitting posture, and the posture change detector 530 detects that that the user's current measurement posture matches the reference posture, the output interface 220 may output a text 66, such as "please maintain the current posture," in a predetermined area of a display 62 of a mobile device 60b. Further, along with the text 66, the output interface 220 may simultaneously or separately output a visual image 67 of the "sitting posture" during estimation of blood pressure.

Once the posture change detector 530 detects that the user's measurement posture matches the reference posture, the estimator 520 may estimate bio-information by using a pre-defined bio-information estimation model, as represented by the above Equation 2, based on the features extracted by the feature extractor 510 from the pulse wave signal 30.

Figure 7:
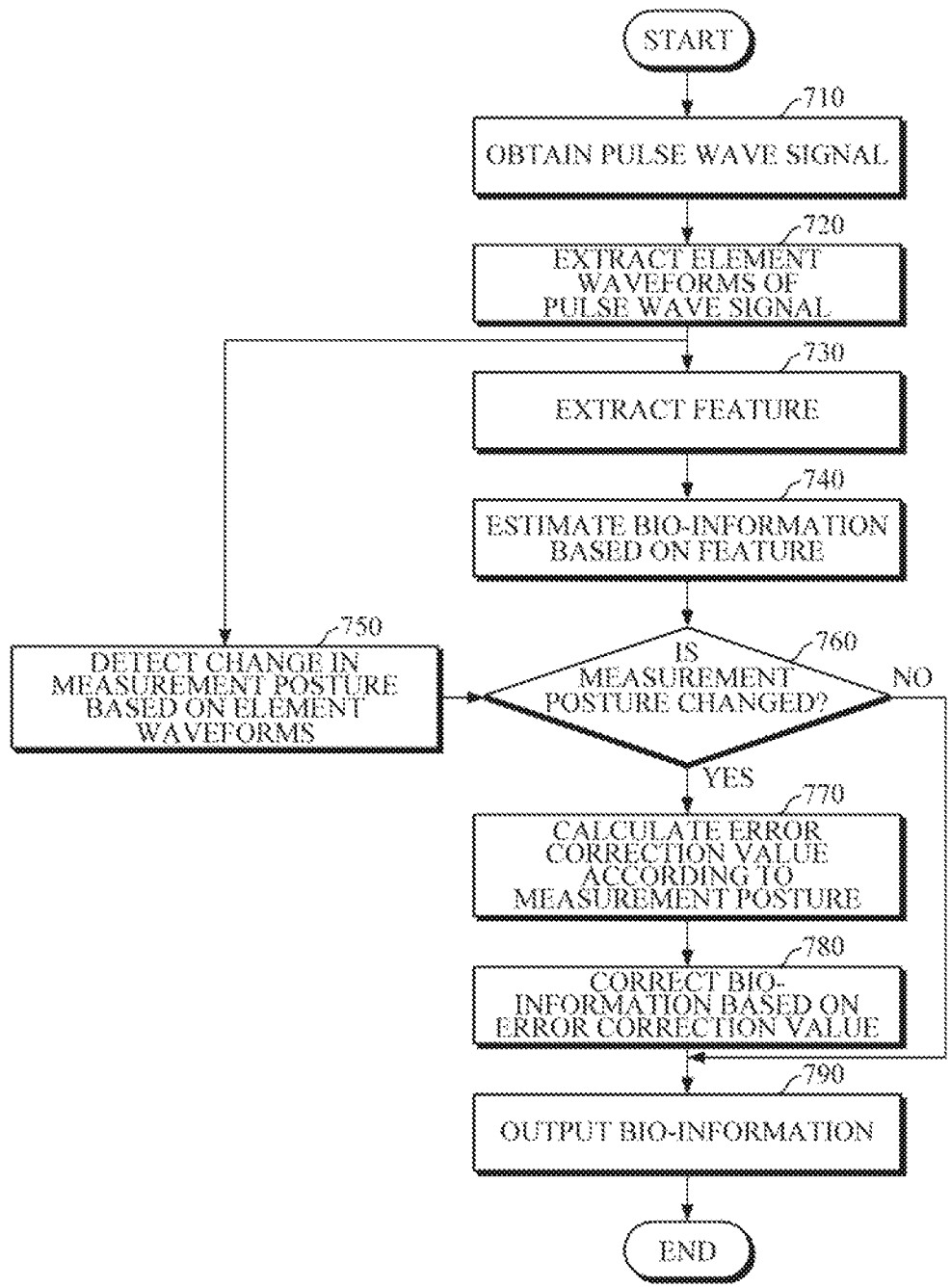
FIG. 7 is a flowchart illustrating a method of estimating bio-information according to an example embodiment.

FIG. 7 is a flowchart illustrating a method of estimating bio-information according to an example embodiment. The method of FIG. 7 is an example of a method of estimating bio-information which is performed by the apparatuses 100 and 200 for estimating bio-information according to the example embodiments of FIGS. 1 and 2. Various example embodiments thereof are described above in detail, and thus will be briefly described below.

Upon receiving a request for estimating bio-information, the apparatuses 100 and 200 for estimating bio-information may obtain a pulse wave signal 30 from an object in operation 710. The apparatuses 100 and 200 may provide an interface for a user, and may receive the request for estimating bio-information input by the user through the interface. Alternatively, the apparatuses 100 and 200 may communicate with an external device, to receive the request for estimating bio-information from the external device.

Then, by analyzing a waveform of the obtained pulse wave signal 30, the apparatuses 100 and 200 may extract components of a plurality of element waveforms which constitute the waveform of the pulse wave signal 30 in operation 720. The waveform of the pulse wave signal 30 is generally formed by superposition of a propagation wave, which moves from the heart to the distal end of the body or branching points in the blood vessels by blood ejection from the left ventricle, and reflection waves which return from the distal end of the body or the branching points of the blood vessels. By analyzing the waveform of the pulse wave signal 30, the apparatuses 100 and 200 may extract components of individual element waveforms related to the propagation wave and/or the reflection waves, e.g., time and amplitude information of the propagation wave and/or the reflection waves.

Subsequently, the apparatuses 100 and 200 may obtain cardiovascular features by analyzing the waveform of the pulse wave signal 30 in operation 730. In particular, the cardiovascular features may include a feature associated with cardiac output (CO) and a feature associated with total peripheral resistance (TPR). For example, the apparatuses 100 and 200 may extract, as features for estimating bio-information, the components of the element waveforms which are extracted in operation 720, a total or partial area under the waveform of the pulse wave signal 30, a maximum amplitude value of the waveform of the pulse wave signal 30, time and/or amplitude values located at the right and left points of the maximum amplitude point and having a predetermined ratio to the maximum amplitude value, a heart rate, or a combination of the extracted information items.

Next, the apparatuses 100 and 200 may estimate bio-information based on the extracted cardiovascular features in operation 740. Upon extracting various cardiovascular features in operation 730, the apparatuses 100 and 200 may estimate bio-information by using a pre-defined bio-information estimation model.

Then, based on the plurality of element waveforms extracted in operation 720, the apparatuses 100 and 200 may detect whether a measurement posture is changed compared to a reference posture in operation 750. For example, the reference posture may be set for each user at a calibration time.

Subsequently, upon detecting a user's measurement posture in operation 750, the apparatuses 100 and 200 may determine whether the measurement posture is changed to a posture, which affects an estimated bio-information value, compared to the reference posture in operation 760. For example, if a time interval between the element waveforms obtained in operation 720 exceeds a predetermined threshold value, the apparatuses 100 and 200 may determine that the user's measurement posture is changed to a posture which causes a fall in blood pressure due to mechanism of fall of blood pressure. Alternatively, by further considering heart rate information, if a time interval between the element waveforms exceeds a first threshold value, and if a variation in heart rate measured in the current measurement posture, compared to a heart rate measured in the reference posture, is less than a second threshold value, or a value obtained by normalizing the variation in the heart rate using the heart rate in the reference posture is less than a second threshold value, the apparatuses 100 and 200 may determine that the user's measurement posture is changed to a posture which causes a fall in blood pressure.

Next, upon determining in operation 760 that the measurement posture is changed, the apparatuses 100 and 200 may calculate an error correction value according to the measurement posture in operation 770. In particular, the apparatuses 100 and 200 may calculate the error correction value based on time intervals between the element waveforms and/or the variation in the heart rate in the measurement posture compared to the heart rate in the reference posture, or a value obtained by normalizing the variation in the heart rate.

Then, based on the error correction value calculated in operation 770, the apparatuses 100 and 200 may obtain a final estimated bio-information value in operation 780 by correcting the bio-information value estimated in operation 740. Upon determining in operation 760 that the measurement posture is not changed, the apparatuses 100 and 200 may obtain the estimated bio-information value, which is estimated in operation 740, as a final estimated bio-information value without error correction.

Subsequently, the apparatuses 100 and 200 for estimating bio-information may output a bio-information estimation result in operation 790. The apparatuses 100 and 200 for estimating bio-information may provide a user with the bio-information estimation result, the user's health information analyzed using the estimation result, and the like, by using various output modules such as a display, a haptic device, a speaker, and the like.

Figure 8:
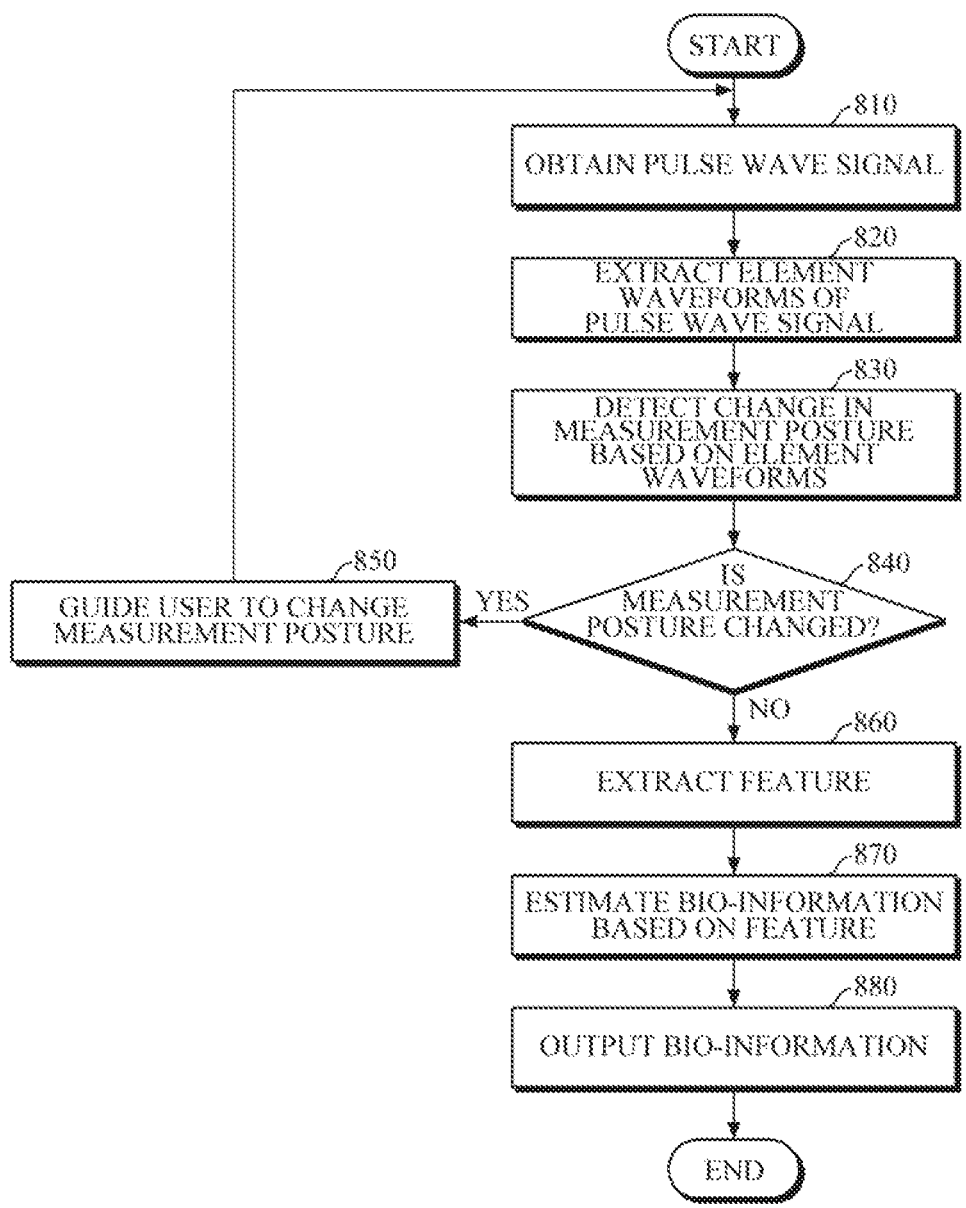
FIG. 8 is a flowchart illustrating a method of estimating bio-information according to another example embodiment.

FIG. 8 is a flowchart illustrating a method of estimating bio-information according to another example embodiment. The method of FIG. 8 is an example of a method of estimating bio-information which is performed by the apparatuses 100 and 200 for estimating bio-information according to the example embodiments of FIGS. 1 and 2. Various example embodiments thereof are described above in detail, and thus will be briefly described below.

Upon receiving a request for estimating bio-information, the apparatuses 100 and 200 for estimating bio-information may obtain a pulse wave signal 30 from an object in operation 810.

Then, by analyzing a waveform of the obtained pulse wave signal 30, the apparatuses 100 and 200 may extract components of a plurality of element waveforms which constitute the waveform of the pulse wave signal 30 in operation 820. By analyzing the waveform of the pulse wave signal 30, the apparatuses 100 and 200 may extract time and amplitude information of individual element waveforms related to the propagation wave and/or the reflection waves.

Subsequently, based on the plurality of element waveforms which are extracted in operation 820, the apparatuses 100 and 200 may detect whether a measurement posture is changed compared to a reference posture in operation 830.

Next, if a user's measurement posture, detected in operation 830, is changed to a posture which affects an estimated bio-information value compared to a reference posture in operation 840, the apparatuses 100 and 200 may guide a user to change the measurement posture in operation 850. In this case, the apparatuses 100 and 200 may provide the user with guide information on the reference posture by using a voice signal or a visual image.

Then, upon determining in operation 840 that a posture, in which an initial pulse wave signal 30 is measured, is not changed, or upon determining in operation 840 that the measurement posture is not changed by guiding the user to change the measurement posture in operation 850 and by re-obtaining the pulse wave signal 30 in operation 810 while the user is in the reference posture, the apparatuses 100 and 200 may extract cardiovascular features for estimating bio-information based on the pulse wave signal 30 in operation 860.

Subsequently, the apparatuses 100 and 200 may estimate bio-information by using the extracted cardiovascular features and a pre-defined bio-information estimation model in operation 870, and may output the bio-information estimation result in operation 880.

Figure 9:
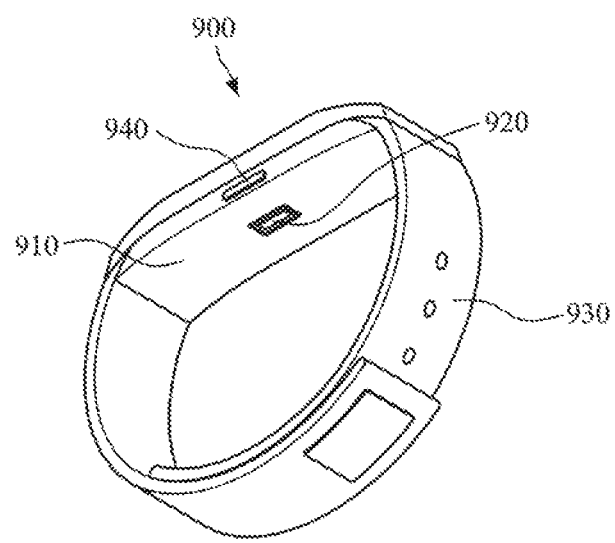
FIG. 9 is a diagram illustrating a wearable device according to an example embodiment.

FIG. 9 is a diagram illustrating a wearable device according to an example embodiment. The aforementioned various example embodiments of the apparatus for estimating bio-information may be mounted in a smart watch worn on a wrist as illustrated in FIG. 9 or a smart band-type wearable device.

Referring to FIG. 9, the wearable device 900 includes a main body 910 and a strap 930.

The main body 910 may be formed to have various shapes, and may include modules which are mounted inside or outside of the main body 910 to perform the aforementioned function of estimating bio-information as well as various other functions. A battery may be embedded in the main body 910 or the strap 930 to supply power to various modules of the wearable device 900.

The strap 930 may be connected to the main body 910. The strap 930 may be flexible so as to be bent around a user's wrist. The strap 930 may be bent in a manner that allows the strap 930 to be detached from the user's wrist or may be formed as a band that is not detachable. Air may be injected into the strap 930 or an airbag may be included in the strap 930, so that the strap 930 may have elasticity according to a change in pressure applied to the wrist, and may transmit the change in pressure of the wrist to the main body 910.

The main body 910 may include a pulse wave sensor 920 for measuring a bio-signal. The pulse wave sensor 920 may be mounted on a rear surface of the main body 910, which comes into contact with the upper portion of a user's wrist, and may include a light source for emitting light onto the skin of the wrist and a detector for detecting light scattered or reflected from the object.

A processor 120, 500 may be mounted in the main body 910. The processor 120, 500 may be electrically connected to various modules, mounted in the wearable device 900, to control operations thereof.

Further, the processor 120, 500 may estimate bio-information by using a pulse wave signal 30 measured by the pulse wave sensor 920. The processor 120, 500 may obtain cardiovascular features by analyzing a waveform of the pulse wave signal 30, and may estimate bio-information by using the obtained features. For example, the processor 120, 500 may obtain the cardiovascular features by using various values, such as time and amplitude values of element waveforms which constitute the waveform of the pulse wave signal 30, a heart rate, a maximum amplitude value, an area of the waveform of the pulse wave signal 30, and the like, and by properly combining the obtained values.

In addition, while being worn on the user's wrist at all times, the wearable device 900 may measure bio-information in various postures of the user. For example, in addition to a case where the user is seated in an upright posture, when the user is seated while leaning back in a chair or lies down while sleeping, the wearable device 900 may also estimate bio-information. However, when calibration is performed while the user is in a seated posture at a calibration time, an error may occur in an estimated bio-information value if the measurement posture is changed.

Accordingly, the processor 120, 500 may detect a posture change at a measurement time compared to a reference posture at the calibration time, and may correct an error in an estimated bio-information value properly according to a change in measurement posture, thereby improving accuracy in estimating bio-information. In this case, by considering a change in a time interval between element waveforms of the pulse wave signal 30 and/or a variation in heart rate according to the change in measurement posture, the processor 120, 500 may estimate a posture change and may calculate an error correction value.

The main body 910 may further include a contact pressure sensor for measuring contact pressure between an object and the pulse wave sensor 920 while the pulse wave signal 30 is measured when the object is in contact with the pulse wave sensor 920. The processor 120, 500 may monitor a contact state of the object based on the contact pressure measured by the contact pressure sensor, and may provide guide information on a contact position and/or a contact state for a user through a display.

Further, the main body 910 may include a storage which stores processing results of the processor 120, 500 and a variety of information. In this case, the variety of information may include reference information for estimating bio-information, as well as information associated with functions of the wearable device 900.

In addition, the main body 910 may also include a manipulator 940 which receives a user's control command and transmits the received control command to the processor. The manipulator 940 may include a power button to input a command to turn on/off the wearable device 900.

A display may be mounted on a front surface of the main body 910, and may include a touch panel for receiving a touch input. The display may receive a touch input from a user, may transmit the received touch input to the processor, and may display a processing result of the processor.

For example, the display may display a bio-information estimation result. In this case, along with the estimation result, the display may display additional information such as a bio-information estimation date, a health condition, and the like. In this case, when a user requests detailed information by operating the manipulator 940 or by performing touch input on the display, the display may display detailed information in various manners.

Moreover, a communication interface, provided for communication with an external device such as a user's mobile terminal, may be mounted in the main body 910. The communication interface may transmit a bio-information estimation result to an external device, e.g., a user's smartphone, to display the estimation result to the user. However, the communication interface is not limited thereto, may transmit and receive a variety of necessary information.

Figure 10:
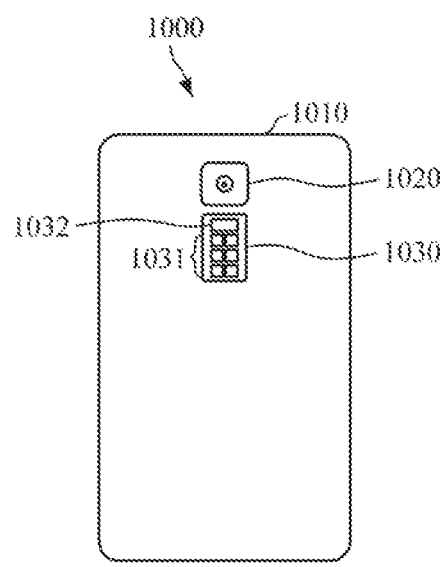
FIG. 10 is a diagram illustrating a smart device according to an example embodiment.

FIG. 10 is a diagram illustrating a smart device, to which example embodiments of an apparatus for estimating bio-information are applied. In this case, the smart device may be a smartphone, a tablet PC, and the like.

Referring to FIG. 10, the smart device 1000 includes a main body 1010 and a pulse wave sensor 1030 mounted on one surface of the main body 1010. In this case, the pulse wave sensor 1030 may include one or more light sources 1031 and a detector 1032. As illustrated in FIG. 10, the pulse wave sensor 1030 may be mounted on a rear surface of the main body 1010, but is not limited thereto, and may be configured in combination with a fingerprint sensor or a touch panel mounted on a front surface of the main body 1010.

In addition, a display may be mounted on a front surface of the main body 1010. The display may visually display a bio-information estimation result and the like. The display may include a touch panel, and may receive a variety of information input through the touch panel and transmit the received information to the processor.

Moreover, an image sensor 1020 may be mounted in the main body 1010. When a user's finger approaches the pulse wave sensor 1030 to measure a pulse wave signal 30, the image sensor 1020 may capture an image of the finger and may transmit the captured image to the processor. In this case, based on the image of the finger, the processor 120, 500 may identify a relative position of the finger with respect to an actual position of the pulse wave sensor 1030, and may provide the relative position of the finger to the user through the display, so as to guide measurement of pulse wave signals with improved accuracy.

By analyzing a waveform of the pulse wave signal 30 measured by the pulse wave sensor 1030, the processor 120, 500 may extract components of individual element waveforms, related to a propagation wave and reflection waves, and/or heart rate information, and by using the extracted components of the element waveforms and/or heart rate information, the processor 120, 500 may detect a change in a user's measurement posture, may correct an error caused by the posture change, may extract features, and the like, and may estimate bio-information based on the obtained information.

The main body 1010 of the smart device 1000 may include a storage which stores reference information and the like for operation of the smart device 1000, including other information input from a user, information obtained by various sensors, information processed by the processor, and other reference information required for estimating bio-information.

Further, the main body 1010 of the smart device 1000 may include a communication interface for communication with various external devices, e.g., a wearable device, a desktop computer, a laptop computer, a tablet PC, a cuff manometer, a smart device of another user, and the like. The processor 120, 500 may control the communication interface to transmit and receive a bio-information estimation result, a variety of reference information, and the like to and from another external device.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing embodiments are merely examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating bio-information, the apparatus comprising:
   a display;
   a pulse wave sensor configured to measure a pulse wave signal from a user; and
   a processor configured to:
   during calibration, control the display to display guide information that directs the user to be placed in a reference posture, and control the pulse wave sensor to measure a reference pulse wave signal that contains heart rate information of the user,
   during a bio-information measurement, measure a current time interval between a plurality of element waveforms of the pulse wave signal, and extract one or more features from the pulse wave signal;
   determine whether a current measurement posture of the user corresponds to the reference posture based on the current time interval of the plurality of element waveforms;
   based on a determination that the current measurement posture does not correspond to the reference posture, obtain an error correction value using a normalized heart rate that is acquired by normalizing a variation of a current heart rate based on a reference heart rate that is measured in the reference posture during the calibration, and estimate the bio-information based on the extracted one or more features and the error correction value; and
   control the display to display the bio-information that is estimated based on the extracted one or more features and the error correction value.

2. The apparatus of claim 1, wherein the processor is further configured to:
    determine a reference time interval between a plurality of reference element waveforms of the reference pulse wave signal that is measured in the reference posture, and
    determine whether the current measurement posture of the user corresponds to the reference posture, based on a difference between the reference time interval and the current time interval.

3. The apparatus of claim 2, wherein the processor is further configured to:
    compare the difference between the reference time interval and the current time interval with a predetermined threshold value, and
    determine that the current measurement posture does not correspond to the reference posture based on the difference between the reference time interval and the current time interval being greater than the predetermined threshold value.

4. The apparatus of claim 2, wherein the processor is further configured to determine whether the current measurement posture corresponds to the reference posture further based on the difference between the current heart rate measured in the current measurement posture and the reference heart rate measured in the reference posture.

5. The apparatus of claim 4, wherein the processor is further configured to:
    compare a first difference between the reference time interval and the current time interval with a first threshold value,
    compare a second difference corresponding to the difference between the current heart rate and the reference heart rate with a second threshold value, and
    determine whether the current measurement posture corresponds to the reference posture, based on comparisons between the first difference and the first threshold value, and between the second difference and the second threshold value.

6. The apparatus of claim 1, wherein the processor is further configured to:
    compare a reference time interval between a peak time T1 of a propagation wave and a peak time T2 of a first reflection wave of the reference pulse wave signal, which are measured when the user is in the reference posture, with the current time interval between a peak time T1' of a propagation wave and a peak time T2' of a first reflection wave of the pulse wave signal, which are measured when the user is in the current posture, and
    determine that the current measurement posture does not correspond to the reference posture, based on a difference between the reference time interval and the current time interval being greater than a predetermined threshold value.

7. The apparatus of claim 1, wherein the plurality of element waveforms comprise at least two of a first element waveform related to a propagation wave, and a second element waveform and a third element waveform related to a reflection wave,
    wherein the processor is further configured to:
        obtain a differential signal of the measured pulse wave signal, and
        obtain times of the plurality of element waveforms by analyzing a local minimum point or a local maximum point of a waveform of the obtained differential signal.

8. The apparatus of claim 1, wherein the processor is further configured to:
    obtain a correction value by applying a first predetermined value to the normalized heart rate and adding a second predetermined value;
    apply a minimum function to the correction value and a third predetermined value to obtain a smaller value between the correction value and the third predetermined value; and
    use the smaller value as the error correction value.

9. The apparatus of claim 8, wherein the processor is further configured to:
    estimate the bio-information by subtracting the error correction value from a scaled value of the extracted one or more features.

10. The apparatus of claim 1, wherein the processor is further configured to, based on the error correction value exceeding a threshold value, change the error correction value to the threshold value.

11. The apparatus of claim 1, wherein the bio-information comprises one or more of blood pressure, vascular age, arterial stiffness, aortic pressure waveform, vascular compliance, stress index, and fatigue level.

12. The apparatus of claim 1,
    wherein the processor is further configured to provide, on the display, guide information for guiding the user to change the current measurement posture to the reference posture, based on the current measurement posture not corresponding to the reference posture.

13. The apparatus of claim 1, further comprising a speaker,
    wherein the processor is further configured to provide, through the speaker, guide information for guiding the user to change the current measurement posture to the reference posture, in response to the current measurement posture not corresponding to the reference posture.

14. A method of estimating bio-information, the method comprising:
    during calibration, displaying guide information that directs a user to be placed in a reference posture, and measuring a reference pulse wave signal that contains heart rate information of the user;
    during a bio-information measurement, obtaining a pulse wave signal from the user, and extracting one or more features from the pulse wave signal;
    measuring a current time interval between a plurality of element waveforms of the pulse wave signal;
    determining whether a current measurement posture of the user corresponds to the reference posture based on the current time interval of the plurality of element waveforms;
    based on a determination that the current measurement posture does not correspond to the reference posture, obtaining an error correction value using a normalized heart rate that is acquired by normalizing a variation of a current heart rate based on a reference heart rate that is measured in the reference posture during the calibration, and estimating the bio-information based on the extracted one or more features and the error correction value; and
    displaying the bio-information that is estimated based on the extracted one or more features and the error correction value.

15. The method of claim 14, wherein the determining whether the current measurement posture corresponds to the reference posture comprises:

determining a reference time interval between a plurality of reference element waveforms of the reference pulse wave signal that is measured in the reference posture; and determining whether the current measurement posture of the user corresponds to the reference posture, based on a difference between the reference time interval and the current time interval.

16. The method of claim 15, wherein the determining whether the current measurement posture corresponds to the reference posture comprises:

comparing the difference between the reference time interval and the current time interval with a predetermined threshold value; and determining that the current measurement posture does not correspond to the reference posture based on the difference between the reference time interval and the current time interval being greater than the predetermined threshold value.

17. The method of claim 15, wherein the determining whether the current measurement posture corresponds to the reference posture comprises determining whether the current measurement posture corresponds to the reference posture further based on a difference between the current heart rate measured in the current measurement posture and the reference heart rate measured in the reference posture.

18. The method of claim 17, wherein the determining whether the current measurement posture corresponds to the reference posture comprises:

comparing a first difference between the reference time interval and the current time interval with a first threshold value;

compare a second difference corresponding to the difference between the current heart rate and the reference heart rate, with a second threshold value; and determining whether the current measurement posture corresponds to the reference posture, based on comparisons between the first difference and the first threshold value, and between the second difference and the second threshold value.

19. The method of claim 14, wherein the estimating the bio-information comprises:

extracting one or more features from the measured pulse wave signal; and estimating the bio-information based on the extracted one or more features.

20. The method of claim 14, wherein the obtaining the error correction value further comprises, based on the error correction value exceeding a threshold value, changing the error correction value to the threshold value.

* * * * *